United States Patent [19]
Stevens

[11] Patent Number: 5,833,662
[45] Date of Patent: Nov. 10, 1998

[54] HEMOSTASIS CANNULA SYSTEM

[76] Inventor: Robert C. Stevens, 18265 NW. Highway 335, Willinston, Fla. 32696

[21] Appl. No.: 374,976

[22] Filed: Jan. 19, 1995

[51] Int. Cl.$^6$ ................................................ A61M 5/178
[52] U.S. Cl. .......................... 609/167; 604/265; 604/164; 600/573; 600/578
[58] Field of Search .................................. 604/167, 164, 604/165, 171, 173, 212, 159, 264, 256, 104, 163, 169, 170, 273; 606/191, 213, 214; 600/573, 575, 576, 577, 585, 578, 579, 581

[56] References Cited

U.S. PATENT DOCUMENTS

| | | | |
|---|---|---|---|
| 3,698,396 | 10/1972 | Katerndahl et al. | 604/164 |
| 3,982,546 | 9/1997 | Friend | 604/173 |
| 4,000,739 | 1/1977 | Stevens . | |
| 4,200,096 | 4/1980 | Charvin | 604/167 |
| 4,430,081 | 2/1984 | Timmermans | 600/579 |
| 4,617,019 | 10/1986 | Fecht et al. | 604/274 |
| 4,629,450 | 12/1986 | Suzuki et al. | 604/167 |
| 4,850,975 | 7/1989 | Furukawa | 604/170 |
| 4,883,461 | 11/1989 | Sawyer | 604/169 |
| 4,904,240 | 2/1990 | Hoover | 604/167 |
| 4,969,875 | 11/1990 | Ichikawa | 604/164 |
| 5,106,376 | 4/1992 | Mononen et al. | 604/158 |
| 5,122,121 | 6/1992 | Sos et al. | 604/274 |
| 5,147,314 | 9/1992 | Vaillancourt | 604/163 |
| 5,154,701 | 10/1992 | Cheer et al. | 604/169 |
| 5,169,387 | 12/1992 | Kronner | 604/164 |
| 5,304,141 | 4/1994 | Johnson et al. | 604/164 |
| 5,322,513 | 6/1994 | Walker | 604/264 |
| 5,425,723 | 6/1995 | Wang | 604/264 |
| 5,584,812 | 12/1996 | Martin | 604/164 |

FOREIGN PATENT DOCUMENTS

| | | | |
|---|---|---|---|
| 546712A2 | 6/1993 | European Pat. Off. | 604/264 |
| 611013A1 | 8/1994 | European Pat. Off. | 604/264 |

*Primary Examiner*—Kien T. Nguyen
*Assistant Examiner*—Justine R. Yu
*Attorney, Agent, or Firm*—Fay Sharpe Beall Fagan Minnich & McKee

[57] ABSTRACT

A hemostasis cannula system includes a cannula, a vessel dilator, an elongate hollow percutaneous needle with clear reservoir, and an obturator. The hemostasis cannula comprises a body having a passage therethrough adapted to receive a catheter as well as a vessel dilator and a specialized obturator. The parts of the system are assembleable in a plurality of configurations including an arrangement for piercing skin, tissue and blood vessels. Another arrangement is adapted for advancing the tubing comprising the cannula, deep within the blood vessel. Lastly, another arrangement is useful for pressure monitoring and fluid introduction directly into the blood vessel of an organism. In the first configuration, the needle is received within the vessel dilator which is in turn received within the tubing comprising the cannula. In the second arrangement, the distal tip needle is withdrawn into the vessel dilator to avoid injury to the vessel when the dilator and cannula are advanced. Lastly, in order to directly monitor the blood pressure, the needle and vessel dilator are replaced with a specialized obturator having a plurality of circumferentially and longitudinally spaced apart openings in fluid communication with the lumen of the obturator as well as with the body of the cannula.

30 Claims, 6 Drawing Sheets

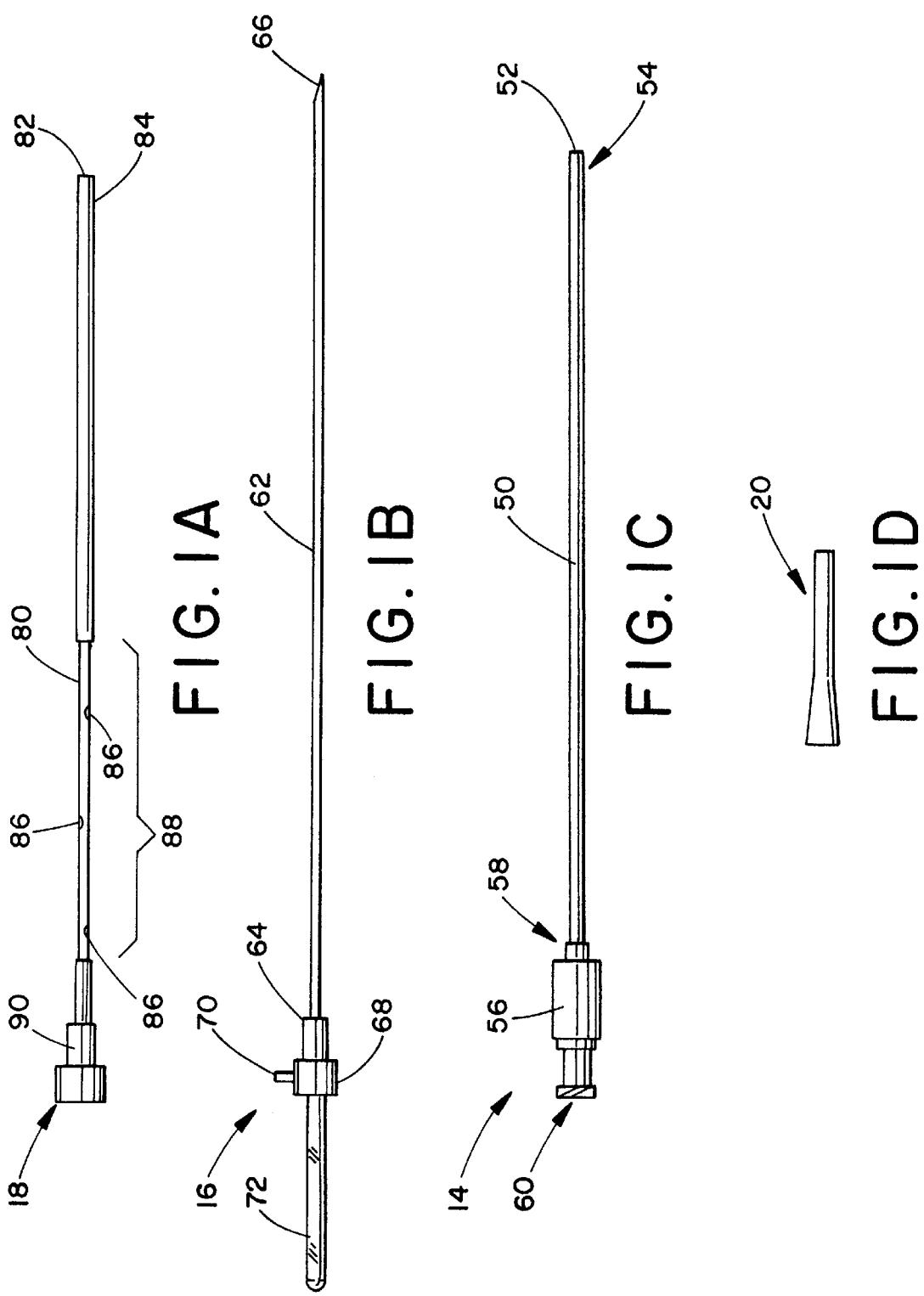

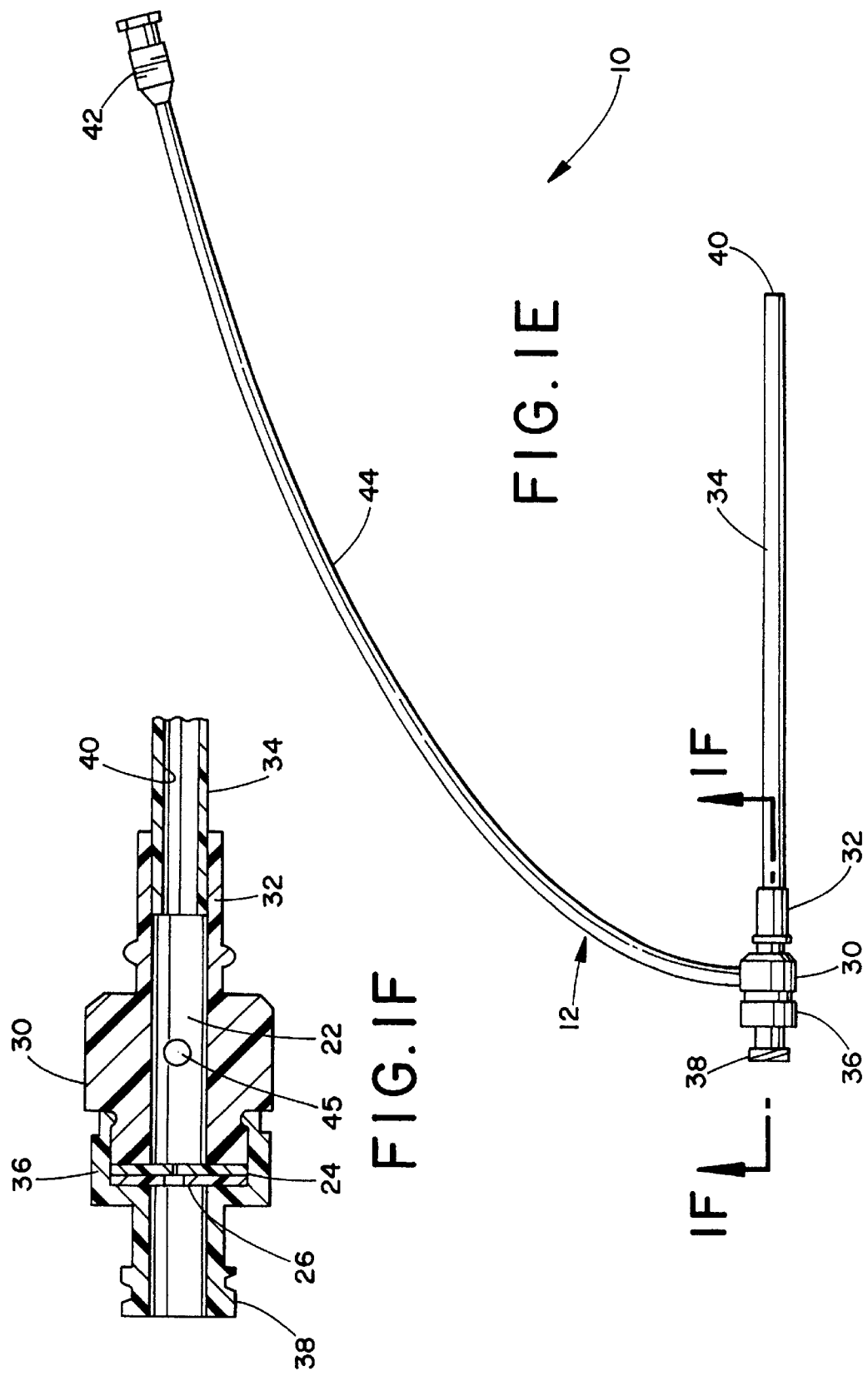

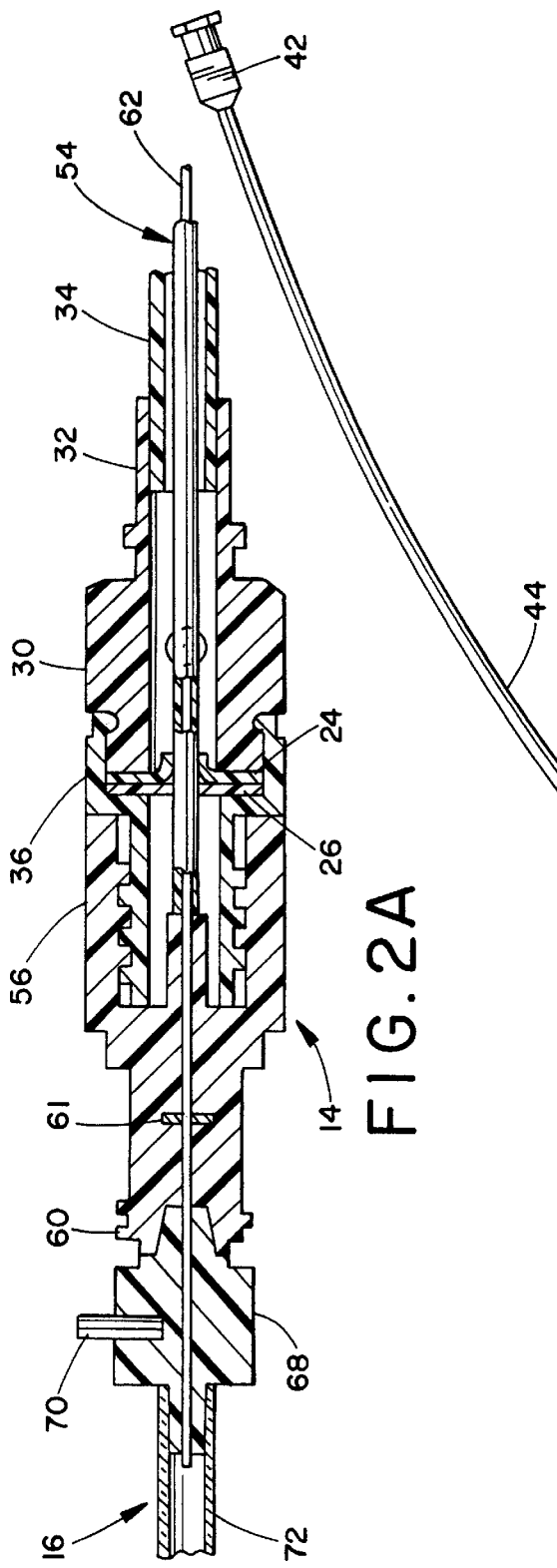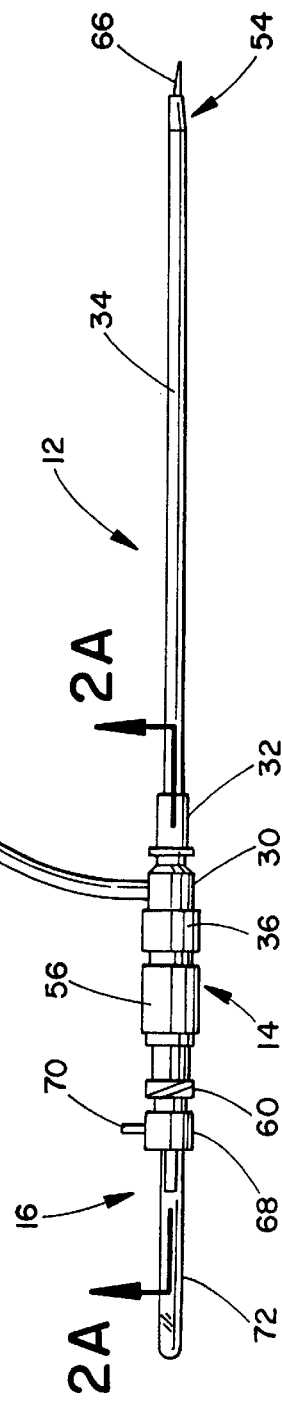

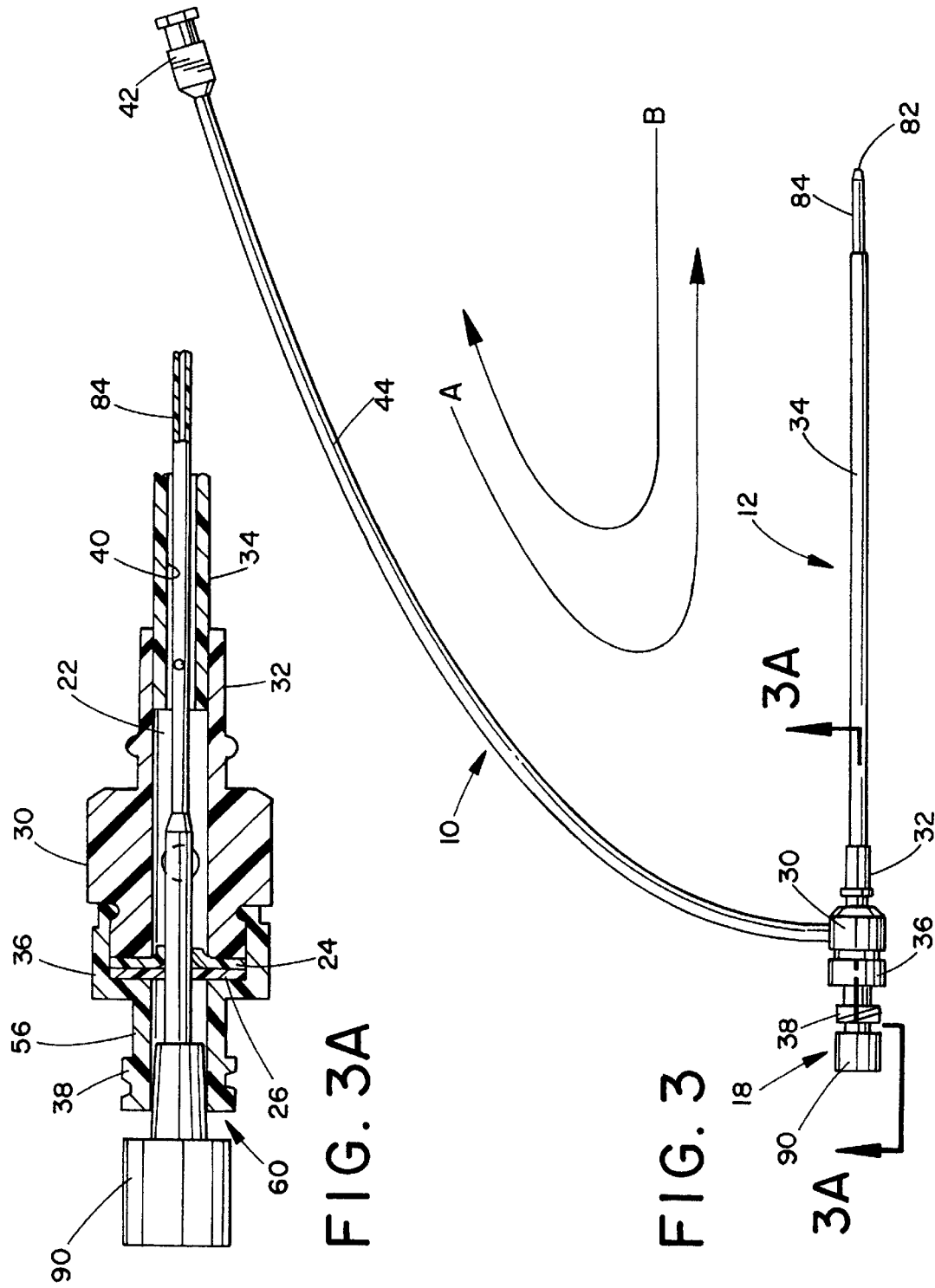

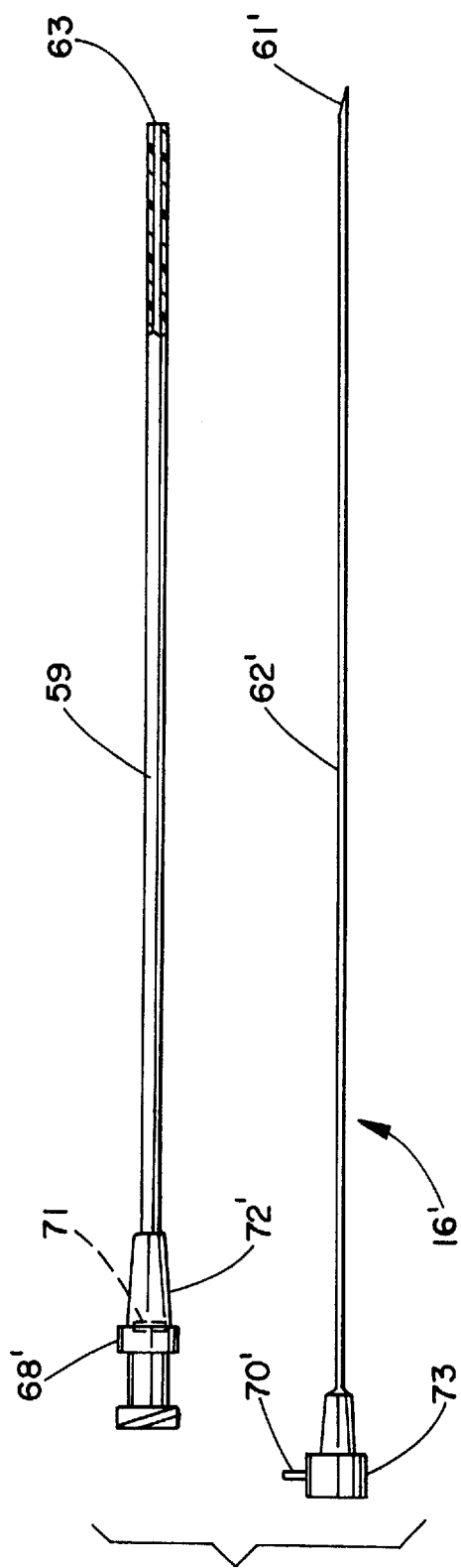

HEMOSTASIS CANNULA SYSTEM

BACKGROUND OF THE INVENTION

The present invention relates to cannulas and their use. The invention is especially concerned with cannulas used for positioning and manipulating intra-vascular catheters known as angiographic catheters.

Angiography is a well-known procedure used to diagnose vascular and organ disease. It involves the introduction of a hollow tubular catheter into one of the major arteries or veins, such as the femoral or brachial arteries, and advancing and maneuvering the catheter tip into smaller branching vessels which are to be studied. After the catheter is in position, a radio-opaque fluid is injected through the catheter into the vascular system to be studied and an X-ray picture is taken of the now X-ray opaque vascular structure.

Prior art techniques for introducing such catheters include what is known as the "cut down" method and various modifications of the "Seldinger" technique. The "cut down" technique involves surgically opening a vein or artery and introducing the angiographic catheter directly through the incision. This method inevitably results in a loss of blood through the incision as well as a need for arterial repair. The use of this method renders it particularly difficult to employ the same vessel when multiple studies are indicated.

*The American Journal of Cardiology*, Vol. 30, September, 1972, at page 378, describes an alternative method of cardiac catheterization, a modification of the Seldinger technique, wherein a percutaneous sheath is introduced into the lumen of a blood vessel. A hollow needle is inserted through the skin and into the lumen; a guide wire is passed through the needle and advanced up the artery or vein into the organ to be studied; the needle is removed, leaving the guide wire in the vessel; a sheath and dilator unit extending from the sheath are together advanced over the wire into the vessel; and, the dilator is removed along with the guide wire. Any type of catheter desired of similar diameter can then be inserted through the sheath into the vessel. To avoid excessive bleeding, and to ensure against the possibility of air embolism, this technique requires the physician to occlude the orifice of the sheath during catheter changes. Various apparatus have been devised for automatically occluding the sheath orifice such as the hemostasis cannula suggested in my earlier U.S. Pat. No. 4,000,739 issued Jan. 4, 1977. Overall however, the above described procedure suffered from the possibility of a blood clot forming at the incision or in the cannula and migrating to the heart, lungs, or extremities. Further, there is some blood loss after the guide wire is withdrawn from the vessel dilator. Although the amount of blood lost is not life threatening, it is unsettling during surgical procedures, especially with the AIDS concern of recent times.

When multiple studies are indicated, it is desirable to maintain the hemostasis cannula lodged in the artery or blood vessel for protracted periods of time, such as over a period of several days. Hemostasis cannulae available at the present often collapse or "kink" due to patient movement during these several days. Further, the possibility of blood clots forming within the hemostasis cannula increase as its presence within the blood vessel continues.

SUMMARY OF THE INVENTION

It is, therefore, an object of the present invention to provide a hemostasis cannula system which is easy to use with very little or no blood loss and which can be left in the vessel during angiographic or other catheterization procedures while the catheter is manipulated within the cannula and vessel and afterwards for extended periods. When the catheter is in place there is no blood loss, yet restriction of catheter manipulation is minimized. A seal capable of withstanding a minimum blood pressure of 300 mm. is provided between the hemostasis cannula and the vessel dilator. Various locking valve arrangements seal the percutaneous needle to the cannula through the dilator. This obviates the necessity of occluding the cannula during the step of piercing the blood vessel thus preventing significant blood loss at all times. The percutaneous needle has a clear reservoir at its proximal end. The reservoir is completely sealed to prevent blood loss while enabling the operator to observe the flow characteristics as well as the color of the blood. These observations are critical to the determination of whether the proper site is located. As an example, the arterial blood is bright red and exhibits a pronounced pulse.

Another object of the present invention is to provide a hemostasis cannula system which, when left in the vessel after angiographic or other catheterization procedures, resists kinking or binding when the patient is ambulatory by means of a specialized obturator. The obturator is received within the hemostasis cannula and fluid-tight locked thereto by a specialized connector. Blood stagnation within the cannula body portion is prevented by flowing a saline solution through the cannula and then through the lumen of the obturator via specialized apertures formed in the obturator. Thus, it is an object of the present invention to provide means by which the hemostasis cannula body and obturator can be flushed at all times or when necessary to prevent clotting within the cannula or at the interface of the cannula and obturator.

Still yet another object of the present invention is to provide a hemostasis cannula system capable of remaining lodged within the blood vessel for a period of several days while providing a mechanism to monitor the blood pressure and other properties or characteristics within the vessel during this period. Injection of medication through the obturator lumen is also contemplated as another object of the invention.

In general, the invention features a hemostasis cannula comprising a body having a passage therethrough adapted to receive a hollow percutaneous needle received within a vessel dilator. The distal tip of the needle extends from the dilator which itself extends beyond the cannula. The needle, dilator and cannula are collectively inserted into the target artery or vessel as a single assembled unit without significant loss of blood. The vessel dilator includes a lumen which is adapted to receive the percutaneous needle provided with the clear sealed proximal reservoir to prevent blood flow when the assembled unit penetrates the blood vessel. The needle and vessel dilator are removable from the hemostasis cannula together and a gasket assembly mounted within the passage of the cannula seals the passage to prevent blood flow. The cannula is further adapted to receive an obturator in place of the needle/dilator pair for preventing collapse of the cannula lumen due to flexing, bending or other movement. The obturator facilitates medication infusion and blood pressure monitoring.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof and wherein:

FIGS. 1A–1E are views in side elevation of the hemostasis cannula system components of the invention arranged in a spaced apart relationship;

FIG. 1F is a cross-sectional view taken on line 1F—1F of FIG. 1E;

FIG. 2 is a view in side elevation of the hemostasis cannula system of FIGS. 1A–1E having various parts thereof assembled into a first arrangement;

FIG. 2A is a cross-sectional view taken on line 2A—2A of FIG. 2;

FIG. 3 is a view in side elevation of the hemostasis cannula system of FIG. 1 having various parts thereof arranged in a second configuration;

FIG. 3A is a cross-sectional view taken on line 3A—3A of FIG. 3;

DETAILED DESCRIPTION OF THE DRAWINGS

Figure 4:
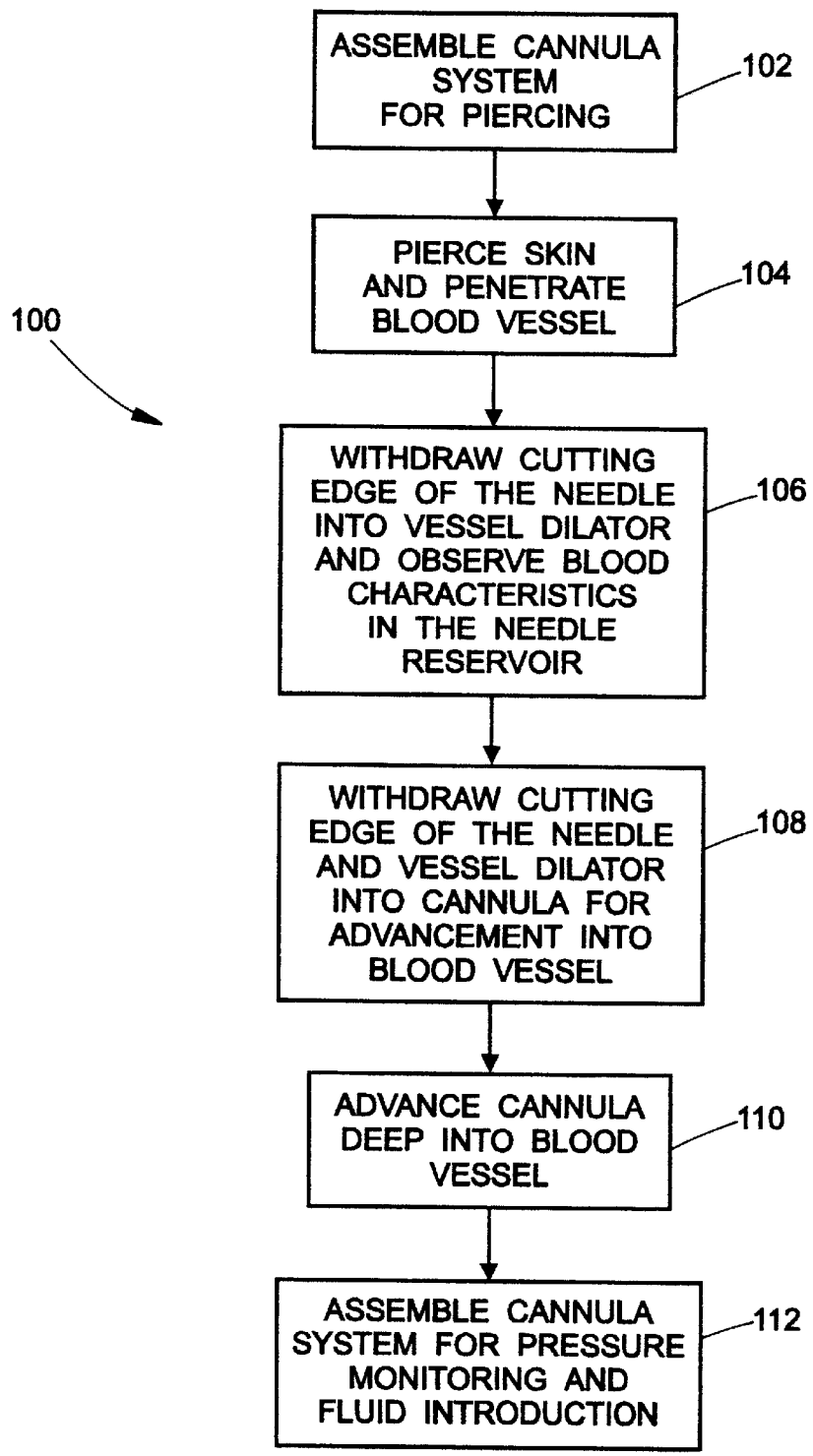
FIG. 4 is a flow chart illustrating a method of using the hemostasis cannula system of FIGS. 1–3 within a blood vessel of an organism; and, FIG. 5 is a view in side elevation of needle assembly alternative to that shown in FIG. 1.

Referring now to the drawings wherein the showings are for the purposes of illustrating the preferred embodiment and method of the invention only and not for the purposes of limiting same, the figures show a hemostasis cannula system 10 comprising a cannula 12, a vessel dilator 14, a needle assembly 16, an obturator 18 and a safety cap 20.

Referring first to FIGS. 1A–1E, the various components comprising the hemostasis cannula system 10 are laid out in a spaced apart relationship to illustrate the relative size and proportions thereof as well as to illustrate the characteristic features of each component of the system. In general, the cannula 12 is configured substantially as described in my earlier U.S. Pat. No. 4,000,739 issued Jan. 4, 1977. More specifically however, cannula 12 includes a generally cylindrical hub or body portion 30 having a tapered region 32 leading to a length of thin-walled flexible tubing 34 on one end and a female Luer lock fitting 36 on the other end. The Luer lock fitting 36 is in fluid communication with the flexible tubing 34 through a passageway 22 formed in the body portion 30 (see FIG. 1F).

As described in my earlier patent, the body portion 30 is made of any one of a number of well-known suitable plastic materials such as polyethylene and includes a pair of juxtaposed internal gaskets 24, 26 (FIG. 1F) which are biased to prevent a flow of fluid from the flexible tubing 34 to the Luer lock fitting 36. The Luer lock fitting includes an enlarged shoulder region 38 which is suitably arranged to engage an operatively associated mating male Luer lock fitting such as provided on the vessel dilator 14 and the obturator 18, both of which will be described in turn and in greater detail below.

The flexible tubing 34 of the cannula 12 defines a lumen 40 which is suitably sized to internally accommodate an operatively associated catheter apparatus for use in such catheterization procedures as angiography and others. The lumen 40 is in fluid communication with the passageway 22 (FIG. 1F) formed in the body portion 30 which, in turn, communicates with an auxiliary female Luer lock fitting 42 through a flexible tube 44 attached to a port 45 of the body portion 30. The auxiliary Luer fitting and flexible tube are useful for the continuous or periodical removal or introduction of fluids such as saline solutions, medications, or dyes into a blood vessel or other organ during surgical procedures and after, for purposes such as to flush the lumen 40 thus preventing blood clots from forming therein. The fitting 42 and tube 44 are also useful in monitoring the blood pressure when the cannula 12 is used in combination with the obturator 18.

With continued reference to FIGS. 1A–1E, the hemostasis cannula system 10 includes a vessel dilator 14 adapted to longitudinally receive a hollow percutaneous needle 62 comprising part of the needle assembly 16. The vessel dilator 14 comprises an elongate hollow tube 50 defining a lumen 52 therethrough for fluid communicating between the distal end 54 of the dilator and a combined male/female Luer lock fitting 56 on the proximal end thereof. The Luer locking fitting 56 includes an integral valve 61 (FIG. 2A) formed of silastic or any other flexible material. Preferably, the valve is molded as a single piece construction well known in the art. Overall, valve 61 functions in a manner similar to the pair of gaskets 24, 26 in the body portion 30 of the cannula 12. More particularly, the valve 61 is punctured or otherwise opened when the percutaneous needle 62 is advanced into the fitting 56 of the dilator 14. The valve prevents the flow of blood through the dilator 14 along the outside of the needle 62. When the needle 62 is withdrawn from the dilator 14, the valve 61 closes in a well known manner to prevent blood loss. The outer diameter of the elongate hollow tube 50 is appropriately sized to be closely accommodated within the lumen 40 of the flexible tubing 34 of the cannula 12. In addition, the elongate hollow tube 50 is slightly longer than the flexible tubing 34 in order to extend beyond the distal tip of the tubing when inserted into the cannula 12 for reasons to be described in greater detail below. The male end 58 of the male/female Luer lock 56 is adapted to engage and fluid tight seal with the Luer lock fitting 36 of the cannula 12. The female end 60 of the male/female Luer lock 56 is adapted to engage and fluid tight seal with a male Luer fitting 64 disposed on the needle assembly 16.

The elongate hollow percutaneous needle 62 includes an angled cutting edge 66 formed on the distal end thereof and further includes a hollow plastic body 68 provided on one end with the male Luer connection 64 which, as described immediately above, engages the male/female Luer lock 56 of the vessel dilator 14 on corresponding mating surfaces. The percutaneous needle 62 is substantially cylindrical in cross section, formed of stainless steel, and is preferably sized according to the dimensions of the lumen 52 formed in the vessel dilator 14 to prevent the flow of blood at the interface thereof. The needle assembly 16 also preferably includes a raised indicia member 70 radially extending from the hollow plastic body 68. The raised member 70 is advantageously disposed on the body 68 in circumferential registration with the angled cutting edge 66. The orientation of the edge 66 is thereby readily evident from a mere visual or tactile observation of the orientation of the member 70. This is useful especially when the edge 66 is hidden from view within the vessel dilator 14. Other orientation indicia are contemplated as well such as a colored marking or a scribe mark on the body 68.

The overall length of the hollow percutaneous needle 62 extending from the body 68 is preferably slightly greater than the length of the vessel dilator 14 in order to expose the cutting edge 66 when the male Luer connection 64 is fully engaged with the male/female Luer lock 56 for reasons to be set forth in greater detail below.

With continued reference to FIGS. 1A–1E, the hollow plastic body 68 of the needle assembly 16 includes a sealed tubular reservoir 72 formed of a clear material, preferably a flexible see-through plastic. The reservoir advantageously allows blood color and flow characteristics to be viewed without spillage or blood loss through the hollow needle and body. When the cutting edge 66 of the needle 62 penetrates a vessel, blood flows through the lumen of the needle 62, through the hollow body 68 and into the closed chamber formed in the reservoir 72. Preferably, the reservoir 72 is large enough to accommodate a sufficient volume of blood to enable a surgeon to adequately assess that the needle reached the target artery. As described above, arterial blood is bright red and pulsates. On the other hand, venous blood appears darker and does not pulse as much. The closed see-through reservoir reduces the burden on a surgeon where, in the past, a finger or other more clumsy mechanism was used to stop the blood flow through the needle before site assessment could be completed.

Lastly in connection with the needle assembly, a clear plastic safety cap 20 is provided for use on the cutting edge 66 to guard against accidental infection to the operator after the needle has been withdrawn from the dilator 14. The safety cap is flexible and adapted to slide over the distal tip of the needle 62 to completely cover the edge 66. A friction fit grip and seal is established between the needle 62 and the lumen of the cap 20 which is preferably sized slightly smaller in inner diameter than the outer diameter of the needle 62.

Lastly with reference to FIGS. 1A–1E, the hemostasis cannula system 10 comprises an obturator 18 which includes an elongate hollow tube 80 defining a lumen 82 for fluid communication between the distal tip 84 thereof and a plurality of apertures 86 formed in side walls of the elongate hollow tube 82. The apertures 86 are preferably formed in a reduced diameter region 88 of the elongate hollow tube 80 in order to permit fluids such as saline solution or medication to flow from the auxiliary Luer fitting 42, through the flexible tube 44 and body portion 30 when the obturator 18 is received within the lumen of the cannula 12. Of course, fluid flow in the reverse direction is also possible.

While the reduced diameter portion allows for flushing or monitoring pressure, the full diameter distal end 84 of the obturator seals the lumen of the flexible tubing 34 against the flow of blood between the obturator 18 and the tubing 34. A male Luer fitting 90 on the proximal end of the obturator 18 is adapted to engage and fluid tight seal the Luer lock fitting 38 of the cannula 12. Further, the fitting 90 seals the lumen 82 closed to prevent fluid flow beyond the body portion 30.

FIG. 5 illustrates a second needle assembly 16' alternative to the preferred needle 16 shown in FIGS. 1A–1E. In practice, some operators prefer to use a solid cutting stylet rather than a hollow needle because of a belief that solid needles are less likely to "core" a hole in a vessel wall. In the alternative needle assembly 16', a hollow steel tube 59 includes a rounded smooth distal opening 63 and a lumen adapted to receive a solid needle 62'. The solid needle 62' has a cutting edge 65' at its distal end. The proximal end of the needle 62' includes a sold male Luer fitting 73. A raised indicia member 70' is disposed on the fitting 73 in a manner to correspond with the position or orientation of the cutting edge 65'. The needle 62' fits snugly within the lumen of the tube 59. The male Luer fitting 73 is adapted to lock onto the proximal end of tube 59 at a hollow body portion 68'. The hollow body portion includes a clear reservoir 72' and an internal silastic valve 71. The valve is preferably molded as a single piece construction according to techniques well known in the art.

In use, the solid needle 62' is inserted into the lumen of the hollow steel tube 59 and the fittings 73 and 68 are connected.

In this position, the cutting edge 65' extends from the tip of tube 59. Together, the needle assembly 16' and cannula 12 are inserted into a blood vessel. Next, the needle 62' is withdrawn from the tube 59 to permit a flow of blood through the lumen of the tube 59 into the clear reservoir 72'. The silastic valve 71 prevents loss of blood while permitting visual inspection of blood characteristics through the reservoir. Also, the valve permits the operator to continue the procedure without the undue burden of capping off the hollow body 68' such as by thumb pressure or other means.

Cannula System Arranged for Piercing Skin, Tissue and Blood Vessel

With reference now to FIGS. 2 and 2A, the hemostasis cannula system 10 is illustrated in a configuration assembled for immediate piercing the skin of an organism with the bloodless percutaneous needle assembly and subsequent insertion of the cannula into a blood vessel or artery. Although the figures illustrate the use of the preferred needle assembly 16, the alternative needle assembly 16' described above may be used as well interchangeably. Preferably, the percutaneous needle 62 is inserted into the lumen of the vessel dilator 14 as illustrated. The male/female Luer lock 56 of the vessel dilator 14 is illustrated connected to the Luer lock fitting 36 of the cannula 12. In addition, the male Luer member 64 of the needle assembly 16 is illustrated connected to the female end 60 of the male/female Luer lock 56. By these connections, the body portion 30 of the cannula 12 is completely sealed to deny the flow of fluids therethrough from either the flexible tubing 34 or the hollow tube of the vessel dilator 14. Fluid flow is possible, however, through the flexible tube 44 via the body portion 30 of the cannula 12. The pair of juxtaposed seals 24, 26 (FIG. 2A) within the body of the cannula, seal the inside surface of the body to the outer surface of the vessel dilator 14 downstream of the tubing 34. Fluid can thus flow from the tubing 34 to the fitting 42 but not beyond the body 30 toward the fitting 36.

In the configuration illustrated in FIG. 2, the cannula system is arranged for piercing the skin, tissue and blood vessel by virtue of the cutting edge 66 extending beyond the distal tip 54 of the vessel dilator 14 which, in turn extends beyond the distal tip of the flexible tube 34. In practice, since the percutaneous needle assembly 16, vessel dilator 14 and cannula 12 are mechanically connected via the Luer fitting arrangements described above and illustrated in FIG. 2, the hemostasis cannula system 10 is functional as a unitary structure. The surgeon simply urges the cutting edge 66 followed by the needle 62 into the tissue of the organism toward the artery or targeted blood vessel. The cutting tip of course pierces the skin and other tissue while the distal tip 54 of the vessel dilator 14 separates and spreads open the tissue in order to create a pathway to accommodate the flexible tubing 34 of the cannula 12.

At this point, a fluid passageway is opened from the blood source through the lumen of the needle 62, vessel dilator 14 and flexible tubing 34. According to standard procedure and practices well-known in the art, the color of the blood flowing into the reservoir 72 is observed in order to determine the correct placement of the cannula system. Generally, in the femoral artery, the blood flow pulsates from the lumen and the color is a bright red. In contradistinction, blood from a vein is usually slower moving and darker in color.

Once the surgeon confirms the targeted vessel to be definitely located and penetrated by the system, the percutaneous needle assembly 16 is unlocked from the cannula system 10 at the Luer member 64. The needle 62 is withdrawn slightly into the tubing 34 in order that the cannula 12 may be further advanced into the target vein without damage thereto. Alternatively, rather than slightly withdrawing the needle into the tubing, a guide wire may be inserted to further advance the cannula 12 into the target vein.

Cannula System Arranged for Advancing Tubing Into Blood Vessel

Once the surgeon has determined that an artery has been located and penetrated by the cannula system 10 by the methods above, and the cutting tip retracted slightly into within the tubing 34, the cannula system is fully inserted up to the tapered portion 32 and advanced deep into the target blood vessel. The vessel dilator 14 and needle assembly 16 are simultaneously withdrawn from the cannula 12 as a single assembly. This is accomplished by unthreading the male end 58 of the male/female Luer fitting 56 from the cannula body portion 30. The valve assembly seals 24, 26 (FIG. 1F) within the body portion 30 prevent the loss of blood through the cannula 12. The cannula, now fully inserted into the target blood vessel, is ready to receive a catheter or other appliance through its lumen for the study or treatment of internal organs or the circulatory system. No blood is lost during the above processes.

Cannula System Arranged for Pressure Monitoring and Fluid Introduction

Referring now to FIG. 3, the hemostasis cannula system 10 is illustrated in a configuration wherein the obturator 18 is inserted into the cannula 12 with the distal tip 84 of the obturator 18 extending slightly beyond the tip of the flexible tubing 34. The outer diameter of the obturator 18 is appropriately sized to be closely received within the lumen of the flexible tubing 34. In addition, the valve assembly seals 24, 26 (FIG. 1F) within the body portion 30 of the cannula 12 provide a fluid tight seal to prevent loss of blood between the tubing and the obturator (FIG. 3A). The male Luer fitting 90 on the obturator 18 engages and fluid tight connects with the female end 60 of the male/female Luer fitting 56. In this manner, blood loss is prevented through the cannula portion.

As indicated above, the obturator 18 includes a lumen 82 to facilitate fluid communication between the target blood vessel or artery and the auxiliary Luer fitting 42 through the flexible hose 44. In addition to the lumen 82 defining a fluid passage, the obturator 18 is provided with a reduced diameter region 88 and a plurality of longitudinally and circumferentially spaced apart apertures 86 (FIG. 1A).

When the pressure in the blood vessel or artery is less than the fluid pressure at the auxiliary Luer fitting 42, fluid flows through the flexible tube 44 in the direction marked A in the figure, into the body portion 30, through the plurality of apertures 86 and out of the lumen 82 into the blood vessel. Conversely, when the blood vessel pressure is greater than the fluid pressure at the auxiliary Luer fitting 42, blood flows in the direction designated B in the figure into the lumen 82, through the apertures 86 body portion 30 and out of the auxiliary Luer fitting 42 through the flexible tube 44. The pressure within the blood vessel is communicated to the fitting 42 through the cannula system 10 under static fluid pressure conditions.

The obturator 18 thus facilitates both fluid introduction such as saline solution or medication as well as a vehicle by which to monitor the blood pressure within the blood vessel. In addition, the obturator 18 mechanically assists the flexible tubing 34 by supporting the walls thereof to prevent kinking or other collapsing or pinching off of the flexible tubing when the cannula 12 is permitted to remain implanted in the patient over extended periods of time such as for several hours or days.

With reference now to FIG. 4, a preferred method of using the hemostasis cannula system of FIGS. 1A–3A will be described. Initially, at step 102, the cannula system 10 is assembled for piercing in order to penetrate the skin, tissue and blood vessel as a single unitary composite. The first end of the vessel dilator is received into the hemostasis cannula followed by the step of receiving the needle assembly with reservoir 72 into the lumen of the vessel dilator. The needle assembly is fluid tight sealed to the vessel dilator which is in turn fluid tight sealed to the hemostasis cannula.

Next, at step 104, the skin is pierced and the blood vessel penetrated by the cutting edge of the needle with reservoir immediately followed by the vessel dilator and cannula. As the needle is advanced into the blood vessel, the vessel dilator provides a tapered interface between the outer diameter of the needle and the flexible tubing of the cannula. In this manner, the skin, tissue and blood vessel are penetrated by the cannula apparatus without damage to the patient.

At step 106, the cutting edge of the needle is retracted slightly into the vessel dilator. As indicated above, the color of the blood flowing into the reservoir 72 is observed through the reservoir whereupon a determination is made as to the correctness of the penetrated vessel.

In order to fully advance the cannula into the blood vessel at step 108, the cutting edge of the needle and vessel dilator are retracted into the tubing 34 of the cannula 12 to ensure that the blood vessel is not damaged by movement of the system within the blood vessel. The cannula system including the flexible tubing, the vessel dilator and the fully retracted needle assembly are advanced deep into the blood vessel at step 110.

Lastly, the needle and vessel dilator are withdrawn from the cannula and replaced with an obturator at step 112. As discussed above, the obturator is elongate and hollow and includes a plurality of apertures which communicate a flow of fluid between the lumen of the obturator and the cannula system. The plurality of holes permit infusion of medications or liquids into the blood vessel through the obturator and further provide for a means by which the blood pressure can be monitored directly. The presence of the obturator within the lumen of the flexible tubing of the cannula prevents the flexible tubing from kinking or otherwise deforming while the cannula system remains installed within a patient. The obturator also occludes the distal portion of the cannula. This keeps blood from entering the cannula which could cause clotting.

The invention has been described with reference to the preferred embodiments. Obviously, modifications and alterations will occur to others upon a reading and understanding of this specification. It is my intention to include all such modifications and alterations insofar as they come within the scope of the appended claims or the equivalents thereof.

Having thus described the invention, I now claim:

1. A hemostasis cannula system for piercing tissue and penetrating a blood vessel of an organism comprising:

a cannula body having a passage therethrough adapted to receive a catheter;

a first length of hollow flexible tubing having a proximal end in fluid-tight engagement with said cannula body and an open distal end;

a hollow dilator received in a lumen of said tubing, the hollow dilator having a distal end extending beyond the open distal end of the flexible tubing;

a fluid control valve in a lumen of the hollow dilator, the fluid control valve being adapted to prevent a flow of blood through said lumen of the hollow dilator;

an elongate hollow needle received through said fluid control valve and in the lumen of said dilator, the elongate needle having a distal end extending beyond the the dilator; and a sealed reservoir on a proximal end of the needle, the sealed reservoir being in fluid communication with a lumen of the needle and being transparent for viewing color and pulsation of blood in the reservoir.

2. The hemostasis cannula system according to claim 1 wherein a proximal end of the hollow dilator includes a fitting in fluid-tight engagement with said body.

3. The hemostasis cannula system according to claim 2 wherein a proximal end of said needle includes a fitting in fluid-tight engagement with the proximal end of said dilator.

4. The hemostasis cannula system according to claim 1 wherein said elongate needle is selectively removable from said dilator.

5. The hemostasis cannula system according to claim 1 wherein the sealed reservoir is a transparent reservoir for viewing the blood from within a blood vessel.

6. The hemostasis cannula system according to claim 1 wherein the sealed reservoir is fixed to a proximal end of the elongate hollow needle.

7. The hemostasis cannula system according to claim 1 wherein the sealed reservoir has a constant volume and is impermeable to blood and air.

8. A hemostasis cannula system comprising:

a body having a passage therethrough adapted to receive a catheter;

a first length of hollow flexible tubing having a proximal end in fluid-tight engagement with said body and an open distal end; and, an elongate hollow obturator received in a lumen of said first length of hollow flexible tubing with a proximal end of the obturator in fluid-tight engagement with said body and a distal end in fluid tight engagement with said lumen of the flexible tubing at the distal end of the flexible tubing to prevent blood from entering between said lumen of the flexible tubing and said distal end of the obturator, the obturator including at least one orifice disposed between said proximal and distal ends of the obturator in a side wall of the obturator, the at least one orifice in fluid communication with i) a lumen of the elongate hollow obturator and ii) said passage in said body.

9. The hemostasis cannula according to claim 8 wherein said at least one orifice includes a plurality of longitudinally and circumferentially spaced apart openings in said elongate hollow obturator.

10. The hemostasis cannula according to claim 9 wherein said body includes a port for communicating a flow of fluids into the body, through said plurality of longitudinally and circumferentially spaced apart openings and through the lumen of said elongate hollow obturator.

11. The hemostasis cannula system according to claim 8 wherein a center portion of the obturator has a diameter which is smaller than a diameter at a distal end of the obturator and smaller than a diameter at the proximal end thereof.

12. The hemostasis cannula system according to claim 11 wherein the at least one orifice is formed in the center portion of the obturator.

13. The hemostasis cannula system according to claim 12 wherein a chamber is formed between an inside surface of the body passage, an inside surface of the hollow flexible tubing, and an outside surface of the center portion of the obturator for communicating a flow of fluid from the at least one orifice to a port formed in the body.

14. The hemostasis cannula system according to claim 8 wherein a chamber is formed between an inside surface of the body passage, an inside surface of the hollow flexible tubing, and an outside surface of the obturator for communicating a flow of fluid from the at least one orifice to a port formed in the body.

15. The hemostasis cannula system according to claim 14 wherein the body includes a port connectable to an operatively associated source of fluid for delivering the fluid to the obturator.

16. A hemostasis cannula system comprising:

a body having a passage extending longitudinally therethrough adapted to receive a catheter, and a port transverse to and communicating with the passage;

a valve provided within said passage to control blood loss through the body;

a hollow flexible tube having a proximal end in fluid-tight engagement with said body;

a dilator removably receivable within said passage of said body and a lumen of said tube;

an elongate needle removably receivable within a lumen of said dilator; and a hollow obturator removably receivable within the passage in the body and the lumen of said tube, the obturator including at least one orifice in a side wall of the obturator for providing fluid communication between a lumen of the obturator and the port of the body.

17. The hemostasis cannula system according claim 16 wherein the elongate needle includes a transparent sealed reservoir fixed to a proximal end thereof for viewing blood color and pulsation.

18. The hemostasis cannula system according to claim 16 wherein the obturator has a diameter at a center portion thereof which is smaller than a diameter at a distal end of the obturator and a diameter at the proximal end thereof.

19. The hemostasis cannula system according to claim 18 wherein the at least one orifice is formed in the center portion of the obturator.

20. The hemostasis cannula system according to claim 19 wherein a chamber is formed between an inside surface of the body passage, an inside surface of the hollow flexible tubing, and an outside surface of the center portion of the obturator for communicating a flow fluid from the at least one orifice to the port formed in the body.

21. The hemostasis cannula system according to claim 16 wherein a chamber is formed between an inside surface of the body passage, an inside surface of the hollow flexible tubing, and an outside surface of the obturator for communicating a flow of fluid from the at least one orifice to the port formed in the body.

22. The hemostasis cannula system according to claim 21 wherein the port in the body is connectable to a source of fluids to maintain the obturator in a open state during prolonged use.

23. A hemostasis cannula system comprising:

a cannula body having a passage adapted to receive a catheter, and a port in fluid communication with said passage;

a hollow flexible tube having a proximal end in fluid-tight engagement with said cannula body;

a valve in said passage to control blood loss from the hollow flexible tube through the cannula body; and, interchangeably received in said cannula body, a one of an elongate hollow dilator and an elongate hollow obturator, the hollow obturator including at least one orifice in a side wall of the obturator providing fluid communication between a lumen of the obturator and the port of the cannula body, the hollow obturator further being adapted for fluid tight engagement with a lumen of said flexible tube at a distal end of the flexible tube to prevent blood from entering between said lumen of the flexible tube and said obturator.

24. The hemostasis cannula system according to claim 23 wherein said dilator is adapted to receive an elongate needle within a lumen of the dilator.

25. The hemostasis cannula system according claim 23 further including an elongate needle received in a lumen of said hollow dilator, the elongate needle having a transparent sealed reservoir fixed to a proximal end for viewing blood color and pulsation.

26. The hemostasis cannula system according to claim 23 wherein the obturator has a diameter at a center portion which is smaller than a diameter at a distal end of the obturator and which is smaller than a diameter at the proximal end of the obturator.

27. The hemostasis cannula system according to claim 26 wherein the at least one orifice is formed in the center portion of the obturator.

28. The hemostasis cannula system according to claim 27 wherein a chamber is formed between an inside surface of the cannula body passage, an inside surface of the hollow flexible tubing, and an outside surface of the center portion of the obturator for communicating a flow of fluid from the at least one orifice to the port formed in the body.

29. The hemostasis cannula system according to claim 23 wherein a chamber is formed between an inside surface of the cannula body passage, an inside surface of the hollow flexible tubing, and an outside surface of the obturator for communicating a flow of fluid from the at least one orifice to the port formed in the body.

30. The hemostasis cannula system according to claim 29 wherein the port in the cannula body is connectable to a source of fluids to maintain the obturator in a open state during prolonged use.

* * * * *